United States Patent [19]
Campbell

[11] Patent Number: 5,873,328
[45] Date of Patent: Feb. 23, 1999

[54] PET LEASH WITH LENGTH-LIMITED ELASTIC SECTION

[76] Inventor: William E. Campbell, P.O. Box 1658, Grants Pass, Oreg. 97528

[21] Appl. No.: 10,393

[22] Filed: Jan. 21, 1998

Related U.S. Application Data

[60] Provisional application No. 60/041,643 Mar. 27, 1997.

[51] Int. Cl.[6] .................................................. A01K 27/00
[52] U.S. Cl. ............................................ 119/798; 119/795
[58] Field of Search .................................. 119/792, 795, 119/797, 798

[56] References Cited

U.S. PATENT DOCUMENTS

| | | | |
|---|---|---|---|
| 536,511 | 3/1895 | Cornell | 54/34 |
| 729,912 | 6/1903 | Andrews | 119/781 |
| 986,973 | 3/1911 | Gordon | 54/34 |
| 1,924,596 | 8/1933 | Davis | 119/798 |
| 2,275,701 | 3/1942 | Taylor | 119/798 |
| 2,737,154 | 3/1956 | Michonski | 119/798 |
| 2,911,947 | 11/1959 | Kramer | 119/798 |
| 3,884,190 | 5/1975 | Gurrey | 119/797 |
| 4,488,511 | 12/1984 | Grassano | 119/798 |
| 4,993,366 | 2/1991 | Sager | 119/798 |
| 5,146,876 | 9/1992 | McPhail | 119/798 |
| 5,706,764 | 1/1998 | Irbinskas | 119/792 |
| 5,749,326 | 5/1998 | Jones et al. | 119/798 |

FOREIGN PATENT DOCUMENTS

| | | | |
|---|---|---|---|
| 2673807 | 9/1992 | France | 119/798 |
| 15304 | of 1910 | United Kingdom . | |
| 426081 | 3/1935 | United Kingdom . | |
| 2264219 | 8/1993 | United Kingdom | 119/798 |

Primary Examiner—Michael J. Carone
Assistant Examiner—James S. Bergin
Attorney, Agent, or Firm—Anderson & Adamson

[57] ABSTRACT

A leash assembly for training dogs includes a handle and an elongate strap connected at one end to the handle, the other end being adapted to be connected to a collar worn by the dog. An elastic element has a first length when in a relaxed state and is extensible four inches to a second length when fully extended. The elastic element is attached to the strap with the length of strap between attached ends of the elastic element being substantially equal to the second length. The force required to reach the fully extended state is about 5 pounds or 2.3 kilograms. The elastic element significantly limits the impact of strong, short correctional tugs or jerks on the leash by the trainer.

9 Claims, 3 Drawing Sheets

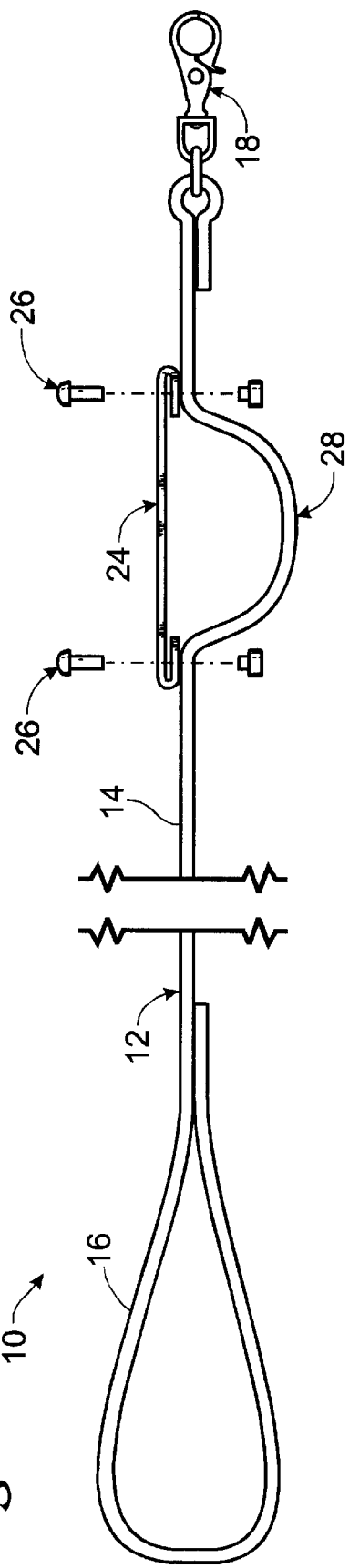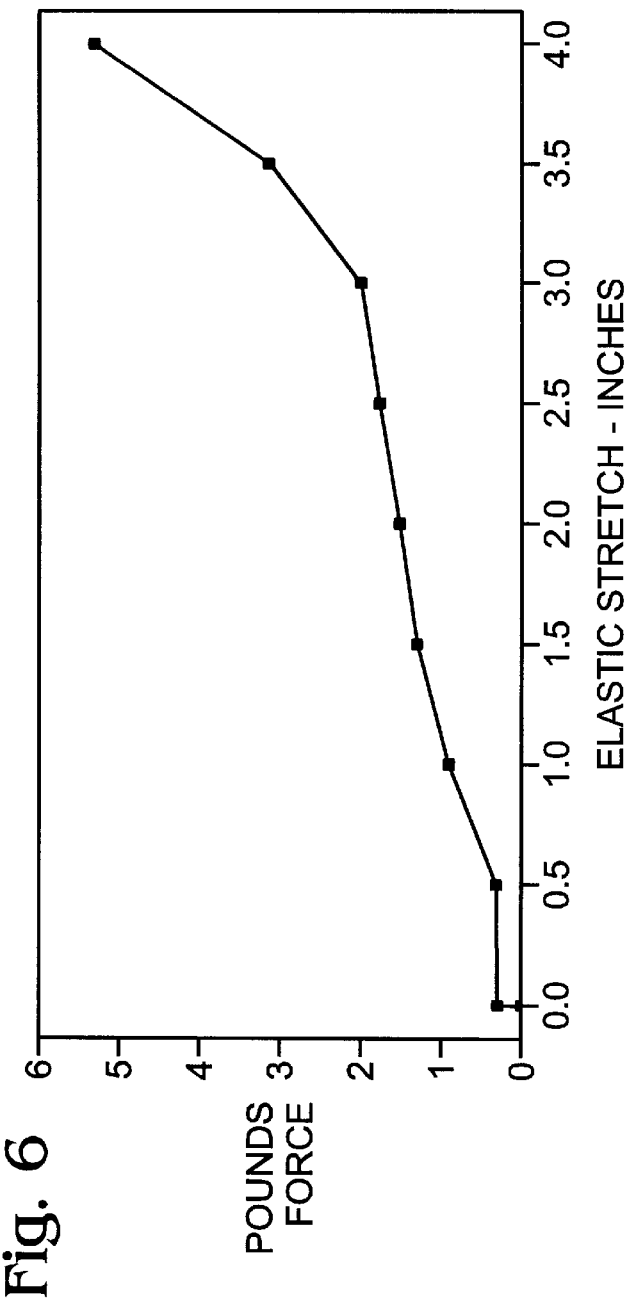

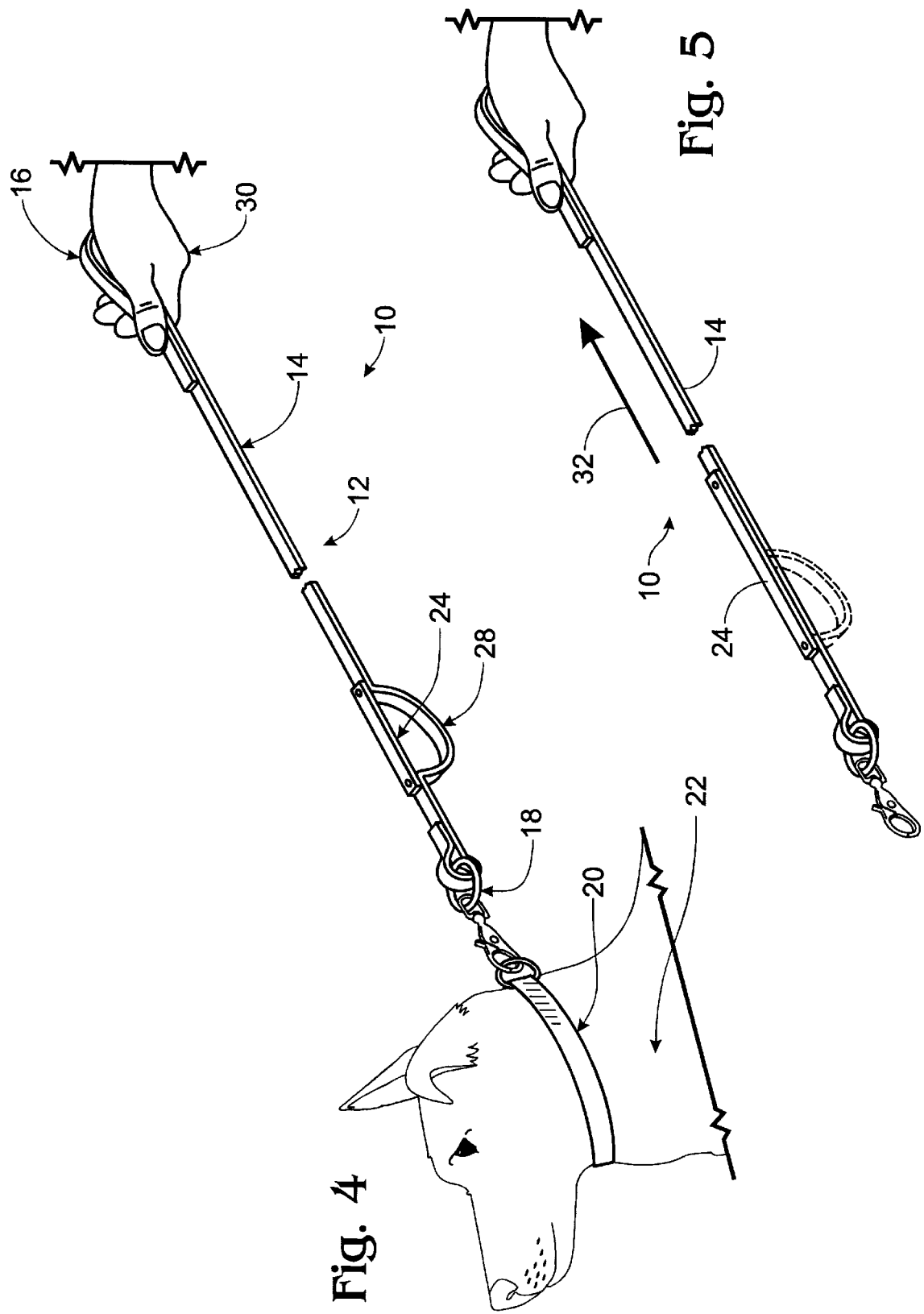

PET LEASH WITH LENGTH-LIMITED ELASTIC SECTION

CROSS-REFERENCE TO RELATED APPLICATIONS

This application claims the benefit of U.S. Provisional application Ser. No. 60/041,643 filed on Mar. 27, 1997.

BACKGROUND OF THE INVENTION

1. Field of the Invention

The present invention relates to the field of animal training leashes or leads, specifically designed to improve their effectiveness while making them less likely to injure animals. In particular, the present invention is directed to such a leash having an elastic section with a limited length of stretch.

2. Description of Related Art

Animal leashes with a shock reducing capacity are known in the art. None of these addresses the specific problem of alleviating the risk of injury to an animal during training exercises or casual restraint by means of an elastic device mounted, during or after manufacture, on a leash connected to an animal's collar, harness, halter, or other device (all referred to generally herein as a "collar").

U.S. Pat. No. 1,924,596 issued to Harry Davis on Aug. 29, 1933 discloses an animal leash having a single elongated cable formed of a strong flexible elastic substance such as rubber.

U.S. Pat. No. 2,275,701 issued to Charles Taylor on Mar. 10, 1942 discloses a dog leash having a tubular sheath encircling an elastic leash strap. The strap is nested in the tubular member which has a handle mounted on the top end and a clip mounted on the bottom end to engage a collar, harness or halter of an animal.

U.S. Pat. No. 2,737,154 issued to George Michonski on Mar. 6, 1956 discloses an expansible dog leash. The leash consists of a handle connected to an elastic cord, the cord having a clip mounted on its end for engaging the collar of an animal.

U.S. Pat. No. 2,911,947 issued to Nelson Kramer on Nov. 10, 1959 discloses a dog leash having a handle connected to a helical spring coil which in turn has a clip mounted on its end for engaging the collar of the dog.

U.S. Pat. No. 3,884,190 issued to Richard Gurrey on May 20, 1975 discloses a resiliently extensible coiled leash. The animal leash is self coiling and is comprised of music wire surrounded by a flexible sheath. A handle and a clip are provided.

U.S. Pat. No. 4,993,366 issued to Thomas Sager on Feb. 19, 1991 discloses a leash consisting of a non-elastic tubular member which houses an elastic bungee cord. The bungee cord is attached inside the none-lastic tubular housing.

U.S. Pat. No. 5,146,876 issued to Gregory E. McPhail on Sep. 15, 1992 discloses an extensible leash having a non-elastic handle connected to an elastic cord and a first non-elastic parallel line. The elastic cord is shorter than the first parallel line which is slidingly connected to a second non-elastic line to which the elastic cord is fixedly connected. The second non-elastic line connects by a clip to the collar of the pet.

BACKGROUND OF THE INVENTION

In traditional formal and informal animal training classes and in literature for puppies and adult dogs, a leash is generally recommended as the primary training tool. Most directions for using leashes instruct a handler or trainer to apply a strong abrupt "jerk " on the leash to correct an animal when it lags behind, forges ahead, fails to obey commands or otherwise displays disobedience.

A conventional training leash is commonly constructed of leather, nylon webbing or cotton webbing which, when quickly extended to the maximum length by an animal's movement or abruptly jerked on or tugged by a handler or trainer, transmits sharp physical impacts of a few pounds to over 16 pounds to an animal's spinal column and/or to the windpipe's tracheal rings. The same impacts are produced when an animal itself suddenly forges ahead against a static leash or lead. These abrupt forces have been found to cause physical injury to an animal's spine, (Anders Hallgren, "Spinal Anomalies in Dogs. " *Animal Behavior Consultant Newsletter*, Vol. 9 No. 3, Jul., 1992) most often by displacing (subluxating) spinal vertebra, or bruising and/or rupturing one or more of the tracheal rings of the windpipe. Standard leashes or leads do not provide an animal with any forewarning that such strong impacts are impending.

These injuries have been found to cause acute and/or long term injury for an animal which can trigger pain and defensive aggression as an injured animal attempts to escape and/or protect itself from further pain. Subsequent casual or formal interactions with adults, children and/or other animals can cause pain or the fear of pain and trigger defensive aggression when an animal turns its head or when its neck or body is manipulated or when it must be examined by medical professionals. These aggressive episodes may be misdiagnosed as idiopathic or spontaneous aggression (of an unrecognized cause) resulting in euthanasia for many animals rather than remedial treatment for physical injury.

SUMMARY OF THE INVENTION

Unlike any of the above devices, our invention allows the manufacture or conversion of any standard leash or lead using a removable elastic member of specific tensile qualities so that it may be used for formal or informal animal training or control while avoiding damage to the animal being trained.

Generally, a leash assembly made according to the invention includes a handle and an elongate strap connected at one end to the handle, the other end being adapted to be connected to a collar worn by an animal, such as a pet dog. An elastic element has a first length when in a relaxed state and is extensible to a second length when substantially fully extended. The elastic element is attached to the strap with the length of strap between attached ends of the elastic element being substantially equal to the second length.

The preferred embodiment of the invention is intended primarily for training dogs. The elastic element has a stretch from relaxed state to fully extended state of four inches. The force required to reach the fully extended state is about 5 pounds or 2.3 kilograms. During use, an animal may by itself learn to ease the tension felt on the collar, halter or harness before the leash or lead reaches full extension. The elastic element also significantly limits the impact of strong, short correctional tugs or jerks on the leash by the trainer.

These and other features and advantages of the present invention will be apparent from the preferred embodiment described in the following detailed description and illustrated in the accompanying drawings.

BRIEF DESCRIPTION OF THE DRAWINGS

FIG. 1 is a side view of a dog leash made according to the invention.

FIG. 4 is an isometric view illustrating training of a dog using the leash of FIG. 1.

FIG. 5 is an isometric view of the leash of FIG. 4 showing extension of the elastic member during training.

FIG. 6 is a chart showing the force required to stretch the elastic member of the leash of FIG. 1.

DETAILED DESCRIPTION OF THE PREFERRED EMBODIMENT

Figure 2:
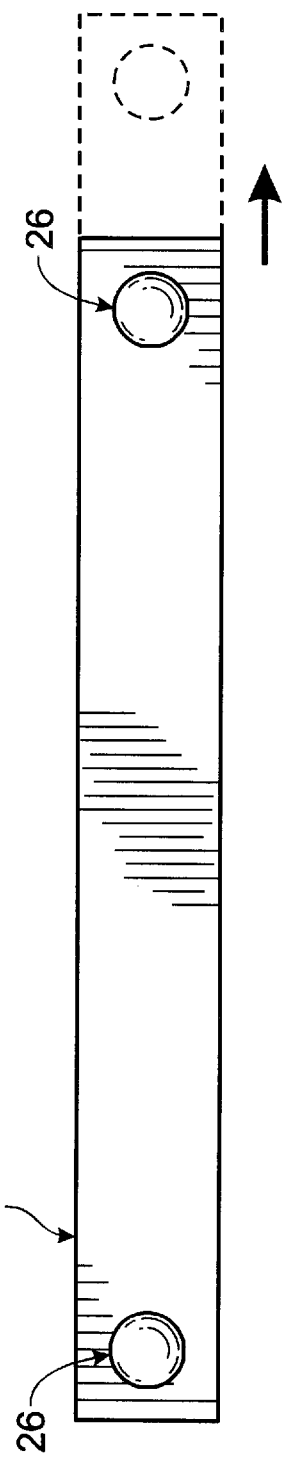
FIG. 2 is a top view of the elastic assembly of the leash of FIG. 1.
Figure 3:
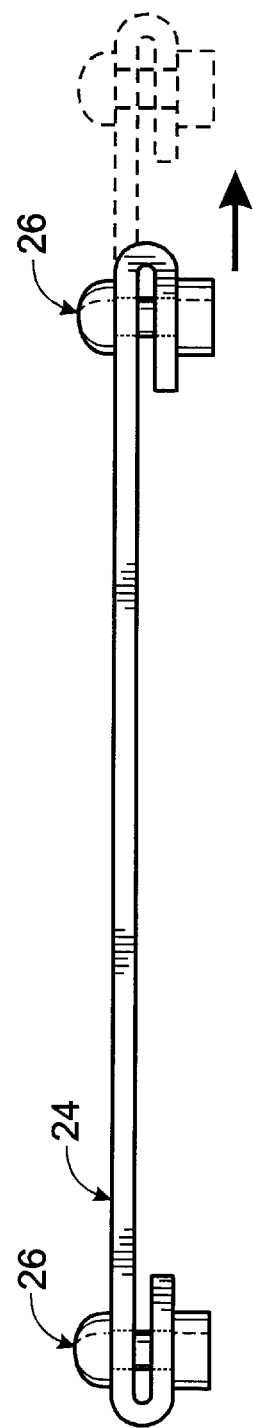
FIG. 3 is side view of the assembly of FIG. 2.

Referring initially to FIGS. 1–3, a leash assembly 10 made according to the invention includes a conventional non-elastic leash 12 having a length of strap 14, also referred to as an inelastic element, with one end formed as a handle 16 and the other end adapted to be connected to a snap 18 for connecting the leash to a collar 20 worn by an animal, such as a pet dog 22 shown in FIG. 4. Each end of an elastic element or cord 24 is attached to strap 14 by a fastener 26. The elastic cord is preferably attached proximate to the leash's snap or other device which connects the leash to the animal's collar. Fasteners 26 may be of any reasonable construction suitable for securing the ends of the cord to the strap. Metal glove snap fasteners sold under the proprietary name KLIKIT™ sockets by Scoville Fasteners Inc. of Clarkesville, Ga. have been found to work well.

The elastic cord may be made of any commercially available elastic materials so long as they provide the characteristics described herein. A preferred cord is a one-half inch braided cord made of 67 percent polyester and 33 percent rubber braided elastic material, and is sold under the proprietary name STRETCHRITE™ by Rhode Island Textile Co. of Pawtucket, R.I. A length of elastic cord is selected that requires a stretch of at least 3 inches (7.6 centimeters), and preferably 4 inches (10.1 centimeters) from a relaxed state to a substantially fully extended state, plus additional unstretched material as required for mounting with the snap fasteners to the strap. The ends of the cord are preferably double folded linearly and then cross-stitched. The cord is fully extended when it becomes taut and there is substantially no increase in length for an incremental increase in force.

Forces within the range of between 2 pounds (0.9 kilograms) and 10 pounds (4.6 kilograms) to fully extend the cord have been found adequate for most domestic animals. Elastic cords requiring smaller forces can be used on smaller animals, such as small breeds of dogs, and correspondingly, elastic cords requiring larger forces can be used on larger animals, such as horses. For training dogs, a cord which requires a force of about 5 pounds (2.3 kilograms) to stretch the cord about 4 inches has been found to be very effective. As shown in the tensile specification chart in FIG. 6, a length of the preferred cord is selected which reaches a fully extended length of about 4 inches with a pull of just over 5 pounds. Specifically, a force of 5.28 pounds results in a stretch of 4.0 inches. Further moderate increases in force do not result in a substantial increase in length.

FIG. 6 shows that less than about 2 pounds of force is required to stretch the cord 3 inches. Beyond 3 inches, the amount of force required to stretch the cord appears to increase asymptotically toward a fully extended length very near 4 inches. This fully extended length thus corresponds to the elastic limit of the cord. This force/distance characteristic of the preferred cord has particular advantages for dog training. As has been mentioned, it is common for a trainer to give a leash a quick jerk with a snap of the wrist, to correct the dog's behavior. That quick jerk, when applied by an adult, is found to have a length of close to 3 inches. When using leash assembly 10, that jerk applies a gradually increasing force to the dog, but stays well below the maximum pull which results when the elastic cord is fully extended and the non-elastic strap applies the force directly. The elastic cord thus serves to dampen the force of the wrist jerk, much as a shock absorber softens the ride in a vehicle.

Leash assembly 10 may be made as a complete leash, or the elastic cord may be attached to a previously made conventional leash, as shown in FIG. 1. The elastic cord is stretched approximately four inches along a corresponding length of a fully extended leash and mounted at each end to the leash strap with snap fasteners 26. When the elastic device is relaxed a slack loop 28 in the leash of four inches is created.

Referring now to FIG. 4, a leash assembly 10 is fastened by the leash snap 18 to an animal's collar. When a trainer's hand 30 applies a correction with a quick jerk of four or fewer inches travel on the leash's handle 16, as shown by arrow 32, the stretching elastic cord transmits a gentle tug to the dog 22 before the leash reaches its full length as shown in FIG. 4. Further, when an animal begins to forge ahead and a trainer stands still and holds the leash handle firmly the gradually increasing resistance of elastic cord 24, as shown in the chart of FIG. 6, conditions the animal on its own to slow or stop to ease the pressure. When first used, the animal will pull the full extent of the elastic cord until the leash strap absorbs the force of the restraint, as is illustrated in FIG. 5. A cord having the characteristics shown in the chart in FIG. 6 provides a smooth transition in restraint force from the elastic cord to the leash strap. Ideally, the elastic cord reaches its maximum length at the same time the leash strap becomes taut, so that any further force is absorbed by the strap, saving the elastic cord from possible damage and making the smoothest possible transition from increasing forces absorbed by the elastic cord to the unforgiving restraint applied by the nonelastic strap.

Mammals possess an innate reflex to oppose physically the direction of forces applied to their bodies. This behavior is called positive thigmotaxis. The stronger the applied force, the stronger is the opposition of the animal. This invention markedly diminishes the danger of injury to an animal's neck by means of mounting to a standard non-elastic leash during or after manufacture a removable elastic element, preferably comprised of polyester and rubber in an appropriate ratio and length, that absorbs the initial shock energy generated as the elastic element nears its full extension, which extension occurs virtually simultaneously with full extension of the leash or lead. The elastic element imparts to an animal that begins to forge ahead a mild but increasing resistance to the animals's neck as the elastic and leash near full extension, in contrast to the sharp impact of a conventional non-elastic leash. This cushioned resistance also provides an animal with a training "cue " that the leash is near its full length, thereby allowing an animal to slow or stop its forging behavior and avoid the impact, albeit diminished, of the fully extended leash. Likewise, when a handler applies an abrupt jerk of less than 4 inches travel as a correction, the cushioned elastic correction replaces the severe impact of a standard leash or lead with a mild increasing pressure prior to full extension, whereby an animal is conditioned to ease or cease its forging.

This gradual shock absorption is a valuable asset to a professional or novice animal trainer for the following reasons:

(1) It alleviates fear of injuring the animal.

(2) A novice trainer learns the technique of the abrupt jerk more quickly, because the invention's cushioned elastic extension provides a cue as to when the jerking or snapping movement of the wrist or arm should be stopped, thereby avoiding full extension of the leash.

(3) When a novice or expert trainer stands still and holds the leash firmly, an animal will be conditioned through trial and error learning to ease its degree of resistance to the leash's slight force.

Although the present invention has been described in detail with reference to a particular preferred embodiment, persons possessing ordinary skill in the art to which this invention pertains will appreciate that various modifications and enhancements may be made without departing from the spirit and scope of the claims as written and as judicially construed under applicable principles of law. The above disclosure is thus intended for purposes of illustration and not limitation.

The invention claimed is:

1. A leash assembly comprising:

a handle;

an elongate inelastic element of a given length connected at one end to the handle, the other end being adapted to be connected to a collar worn by an animal;

an elastic element having a first length when in a relaxed state, the elastic element being extensible to a second length less than the given length when substantially extended to the elastic limit of the elastic element, the ends of the elastic element being attached to the inelastic element with the length of inelastic element between the attached ends of the elastic element being substantially equal to the second length.

2. A leash assembly according to claim 1 wherein the second length is about 4 inches more than the first length.

3. A leash assembly according to claim 1 wherein the elastic element is extensible to the second length when extended by a force of less than about 10 pounds.

4. A leash assembly according to claim 1 wherein the elastic element is manually attachable to and removable from the inelastic element.

5. A leash assembly comprising:

a handle;

an elongate inelastic element of a given length connected at one end to the handle, the other end being adapted to be connected to a collar worn by an animal;

an elastic element having a first length when in a relaxed state, the elastic element being extensible to a second length less than the given length and not more than about 4 inches more than the first length when extended by a force of between 2 pounds and 10 pounds, the ends of the elastic element being attached to the inelastic element with the length of inelastic element between the attached ends of the elastic element being substantially equal to the second length.

6. A leash assembly according to claim 5 wherein the elastic element is extensible to the second length when extended by a force substantially equal to about 5 pounds.

7. A leash assembly according to claim 5 wherein the elastic element is manually attachable to and removable from the inelastic element.

8. A method of making a training leash assembly for an animal wearing a collar comprising the steps of:

providing a pet leash having a handle and an elongate inelastic element of a given length connected at one end to the handle, the other end being adapted to be connected to a collar worn by an animal;

providing an elastic element having a first length when in a relaxed state and a second length less than the given length when extended substantially to the elastic limit of the elastic element; and attaching the ends of the elastic element to the inelastic element so that there is a length of inelastic element between the ends of the elastic element substantially equal to the second length.

9. A method according to claim 8 wherein the step of providing an elastic element comprises providing an elastic element in which the second length is about 4 inches more than the first length.

* * * * *